(12) United States Patent
Schoen et al.

(10) Patent No.: US 8,556,198 B2
(45) Date of Patent: Oct. 15, 2013

(54) GLASS POWDER HAVING GRAIN SIZE DISTRIBUTION AND PROCESS FOR THE PRODUCTION THEREOF

(75) Inventors: Bastian Schoen, Landshut (DE); Ewald Mittermeier, Altfraunhofen (DE); Yvonne Pfluegler, Landshut (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 13/452,153

(22) Filed: Apr. 20, 2012

(65) Prior Publication Data

US 2012/0295111 A1    Nov. 22, 2012

(30) Foreign Application Priority Data

Apr. 21, 2011 (DE) .................. 10 2011 100 959

(51) Int. Cl.
*B02C 17/20* (2006.01)
(52) U.S. Cl.
USPC .......................................... 241/21; 241/24.3
(58) Field of Classification Search
USPC .............. 241/21, 184, 171, 172, 24.3; 501/11
See application file for complete search history.

(56) References Cited

U.S. PATENT DOCUMENTS

| | | | |
|---|---|---|---|
| 3,791,523 A * | 2/1974 | Okumura et al. | 210/198.3 |
| 5,145,520 A * | 9/1992 | Kokubo et al. | 106/35 |
| 5,340,776 A * | 8/1994 | Paschke et al. | 501/11 |
| 6,623,856 B1 | 9/2003 | Kodas et al. | |
| 6,634,576 B2 * | 10/2003 | Verhoff et al. | 241/21 |
| 2010/0130666 A1 * | 5/2010 | Hart et al. | 524/494 |

FOREIGN PATENT DOCUMENTS

| | | |
|---|---|---|
| CN | 1771208 | 5/2006 |
| CN | 101094818 | 12/2007 |
| DE | 4100604 | 2/1992 |
| DE | 102009008954 | 10/2010 |
| EP | 1005911 | 6/2000 |

OTHER PUBLICATIONS

Office Action dated Mar. 1, 2012 corresponding to German Patent Application No. 10 2011 100 959.4.
Office Action dated Apr. 1, 2013 corresponding to Chinese Patent Application No. 201210113413.1, 7 pp.
Office Action dated May 29, 2013 corresponding to German Patent Application No. 10 2012 203 875.2, 10 pp.

* cited by examiner

*Primary Examiner* — Mark Rosenbaum
(74) *Attorney, Agent, or Firm* — Ohlandt, Greeley, Ruggiero & Perle, LLP

(57) ABSTRACT

A glass powder is provided that includes, as the main component, powder particulates of glass having a mean particulate size of less than or equal to 1.5 μm, and which is free of particles having a particle size of greater than 10 μm. A process for the production of such a glass power is also provided. The glass powder is particularly suitable as a filler of plastic dental compositions, in particular dental composites.

12 Claims, 1 Drawing Sheet

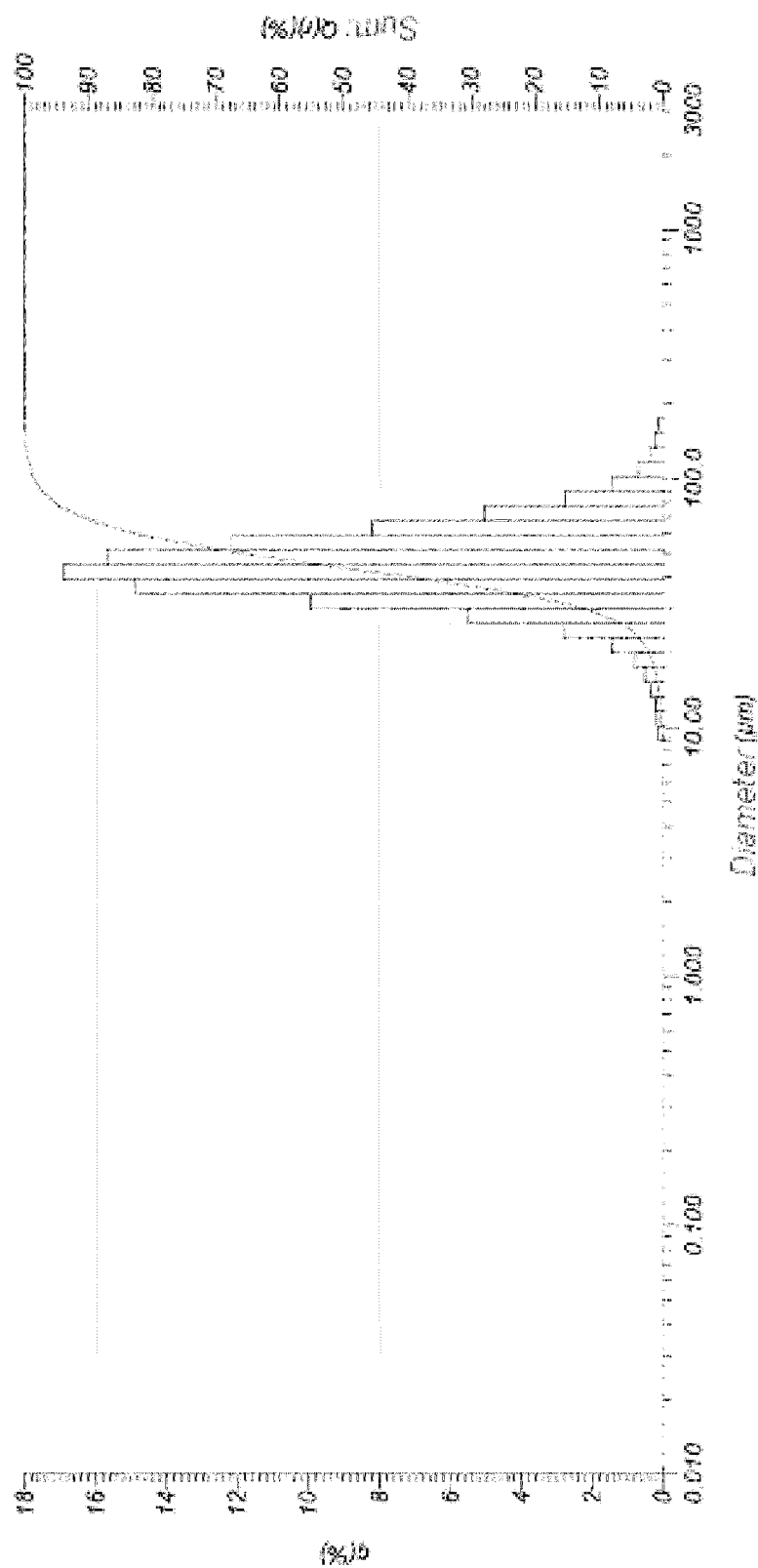

019
GLASS POWDER HAVING GRAIN SIZE DISTRIBUTION AND PROCESS FOR THE PRODUCTION THEREOF

CROSS REFERENCE TO RELATED APPLICATIONS

This application claims benefit under 35 U.S.C. §119(a) of German Patent Application No. 10-2011-100-959.4, filed Apr. 21, 2011, the entire contents of which are incorporated herein by reference.

BACKGROUND OF THE INVENTION

1. Field of the Invention

Glass powders can be used for various applications. One of these is the dental sector, in which plastic dental compositions are increasingly being used for dental restoration. These plastic dental compositions usually consist of a matrix of organic resins and various inorganic fillers. The inorganic fillers predominantly consist of powders of glasses, (glass-) ceramics, quartz or other crystalline substances (e.g. $YbF_3$), sol-gel materials or Aerosils, and they are added to the plastic composition as filling material.

2. Description of Related Art

The use of plastic dental compositions is intended to avoid possible harmful side-effects of amalgam and to achieve an improved aesthetic impression. Depending on the plastic dental compositions selected, they can be used for different dental restoration measures, for example for tooth fillings and also for securing parts, such as crowns, bridges and inlays, onlays etc.

The filling material per se is intended to minimize the shrinkage caused by the polymerization of the resin matrix during curing. For example, if there is a strong adhesion between tooth wall and filling, excessive polymerization shrinkage can lead to the tooth wall breaking. If the adhesion is inadequate, excessive polymerization shrinkage may result in the formation of peripheral gaps between tooth wall and filling, which can promote secondary caries. Furthermore, certain physical and chemical demands are imposed on the fillers.

It must be possible to process the filling material to form powders that are as fine as possible. The finer the powder, the more homogeneous the appearance of the filling. At the same time, the polishing properties of the filling are improved, which in addition to reducing the surface area available for attack also leads to improved resistance to abrasion and therefore to a longer-lasting filling. To enable the powders to be processed successfully, it is also desirable for the powders not to agglomerate.

Furthermore, the refractive index and colour of the plastic dental composition in its entirety and therefore also of the filler should be as well matched as possible to the natural tooth material, so that it is as far as possible indistinguishable from the surrounding, healthy tooth material. The grain size of the pulverized filler being as small as possible also plays a role in this aesthetic criterion.

Further properties are desirable and known to a person skilled in the art and are described in more detail, for example, in DE 102009008954 B4.

Among plastic dental compositions, a distinction also needs to be drawn between dental cements and composites. In the case of dental cements, also known as glass ionomer cements, the chemical reaction of the fillers leads to curing of the dental composition, and consequently the curing properties of the dental composition and therefore the workability thereof are influenced by the reactivity of the fillers. This often involves a setting process which is preceded by a radical surface curing, for example under the action of UV light. Composites, also referred to as filling composites, contain, by contrast, fillers which are as chemically inert as possible, since their curing properties are determined by components of the resin matrix itself and a chemical reaction of the fillers is often disruptive for this.

Such a composite filling usually consists of a polymer matrix which, in order to improve the chemical and also the physical properties, can contain up to 90% by weight of an inert filler described. Common organic polymers are mostly dimethacrylates, for example triethylene glycol dimethacrylate (TEGDMA), UDMA, bis-GMA, acrylate, methacrylate, 2,2-bis-[4-(3-methacryloxy-2-hydroxypropoxy)phenyl]propane (bis-GMA), urethanemethacrylate and/or alkanediol dimethacrylate. However, it is also possible to use other polymer resins, e.g. epoxy-based resins, and the mixtures or copolymers thereof.

The plastics used in a plastic dental composition described usually have a refractive index in the range of 1.45 to 1.65. In order to achieve the highest possible transparency of the material, the refractive index of the fillers has to be matched to that of the surrounding matrix. Differences in refractive index between the polymer matrix and the fillers used, and also a difference between the fillers themselves, lead to scattering and reflection at the interfaces, and these result in reduced transparency. The finer the powder, the more homogeneous the appearance of the filling, and therefore also the higher the transparency.

A reduced transparency in the visible wavelength range has a negative effect on the optical appearance of the filling. A high transparency in the UV range is also important, in particular for the processing properties, however. The composite material is usually cured by irradiation with UV light. Common curing lamps have a wavelength range of 380 nm to 515 nm and/or 420 nm to 480 nm. A low transmissivity in the UV spectral range results in a relatively small depth of polymerization. A material with a high UV absorption has to be applied in a plurality of steps, in particular in the case of large layer thicknesses, in order to ensure sufficient polymerization. If this is not the case, the material can be cured in one step. For these reasons, it is advantageous if the filler, i.e. in particular the glass powder, has the smallest possible particle size, since the interaction in the visible and also in the ultraviolet wavelength range decreases with a falling particulate size of the glass powder.

In order to produce a glass powder which is suitable as a dental filler and has high transparency values and a mean particulate size in the micrometer or submicrometer range, special grinding processes are required. For the production of the glass powders by way of such fine grinding processes, use is made of stirred ball mills, vibration mills or bead mills. During grinding, it should be ensured that no disruptive contamination is formed by dust from the mill lining and/or the grinding beads used. Therefore, use is made of glass grinding beads which have matched refractive indices and consist of the same material or a material with the same refractive index as the glass to be ground to form the glass powder. The dust formed during the grinding thus has no negative effects on the optical properties of the filler. For the mill lining, use is made either of ceramics such as $Zr_2O_3$, $Al_2O_3$, SiC or plastics such as polyurethane. In the case of a ceramic lining, only minimal dust is formed. In the case of mills lined, for example, with polyurethane, the plastic dust can be removed again from the powder by a burn-out operation. Such grinding processes are described in detail, for example, in DE 4100604 C1 or EP 1005911 A1.

For the production of glass powders having particulate sizes in the micrometer or submicrometer range by grinding in vibration mills, stirred ball mills or bead mills, grinding beads having a diameter of less than 2 millimeters (mm) are usually used, in order to achieve effective comminution. The grinding beads are accelerated onto one another in the mill and comminute the filling material, i.e. the starting glass of the glass powder to be obtained, when they collide therewith. The grinding process produces a glass powder having particulates with a more or less sharp diameter distribution which generally resembles a Gaussian bell curve. The mean particulate size corresponds to the position of the maximum of the distribution.

In practice, however, it has been found that glass powders produced by the described grinding processes can repeatedly be found to have, in addition to the expected statistical distribution of the particulate size, particles with a significantly greater particle size, which are subject to a further statistical distribution. The statistical grain size distribution of the glass powder over all the components thereof (particulates and/or particles) therefore has at least two maxima in this case.

The diameter of these large particles may be dependent on the size of the grinding beads used, and, in the case of grinding beads having a diameter of less than 2 mm, is about 5 micrometers (µm) to 100 µm. The content of these particles is usually low and can be approximately 1 gram (g) or less per 20 kilograms (kg) of glass powder, but is very disruptive when the glass powder is used as a dental filler, because such particles have a disadvantageous effect on the gloss consistency and also the polishing properties of the plastic dental composition. Over the course of abrasion of the surface, the coarse particles then protrude from the surface of the plastic dental composition or form craters upon complete break out. These irregularities in the surface lead to reduced gloss or a reduced optical quality. The instances of break out can to some extent be identified as small holes with the naked eye. For these reasons, such large particles which fall out of the statistical distribution of the particulate size of the glass powder are undesirable in a glass powder.

SUMMARY

Against this background, it is an object of the invention to provide a glass powder which has an improved grain size distribution, such that, particularly when used as a filler in plastic dental compositions, an improved gloss consistency and the polishing properties of the plastic dental composition are ensured, and also a surface which is free of craters to the greatest possible extent during use for a long time is made possible. It is a further object of the invention to provide a process for producing a glass powder which is free of disruptive large particles.

The inventors recognized that the disruptive large particles which are outside the statistical distribution of the size of the glass powder particulates are formed by breakage and/or spalling of the above-described grinding beads used in the grinding process and/or linings of the mills. The grinding process described further below removes these oversized particles from the glass powder during the grinding process.

The glass powder according to the invention therefore contains, as the main component, powder particulates having a mean particulate size of ≤1.5 µm, and is free of particles having a particle size of >10 µm.

The term "mean particulate size" has been explained above. Within the context of the invention, the term "particulate" refers to components of the desired glass powder which have the desired particulate size, whereas the term "particle" refers to the large disruptive artefacts of the grinding beads and/or linings and/or other constituent parts of the mills which are formed by breakage and/or spalling.

Within the context of the present description, the term "diameter" refers to the maximum extent of the particulate and/or particle. In the case of spherical particulates and/or particles, the diameter is simply the diameter of the sphere. In the case of ellipsoidal or plate-like particulates and/or particles, the diameter is measured at the point of the maximum extent, in the case of an ellipsoid for example at the main axis thereof.

The glass powder contains, as the main component, powder particulates of ground glass having a mean particulate size of at most 1.5 µm. It is similarly possible, and encompassed by the invention, for the glass powder to contain further components, which do not have to consist of glass. By way of example, plastics, for example plastic spherical beads, are conceivable. It is preferable for the main component of the glass powder particulates to be present in the glass powder according to the invention in an order of magnitude of more than 90% by volume. According to the invention, no particles having a particle size of more than 10 µm are present in the glass powder. In the prior art, to date glass powders having particulate sizes of about 0.5 µm to 3 µm have been produced. The trend for use as a dental filler is toward ever smaller particulate sizes, however. Only in the case of these particulate sizes do the disruptive large particles become apparent, because they fall significantly out of the distribution of the diameters of the glass powder particulates.

It is preferable for the mean particulate size in a glass powder according to the invention to be at most 1.0 µm, likewise preferably at most 0.7 µm, particularly preferably less than 0.5 µm and very particularly preferably less than 0.25 µm. According to the invention, no particles having a particle size of more than 10 µm are present in said glass powder, preferably no particles having a particle size of more than 5 µm, particularly preferably no particles having a particle size of more than 3 µm. This applies to all the given mean particulate sizes of the glass powder particulates.

In the process according to the invention for producing the glass powder, in particular the glass powder according to the invention as described above, as the starting material a glass is ground down to the desired mean particulate size in a mill with grinding bodies, which can be in the form of grinding beads. The starting material corresponds at least substantially to the glass, the powder of which is intended to be obtained by the process. It would be possible to take leaching effects during the grinding into account, however. The grinding produces a mixture of the desired glass particulates having a mean particulate size of at most 1.5 µm, which are intended to form the main component of the glass powder, and the disruptive particles. The disruptive particles having a particle size of more than 10 µm are removed from the mixture by separation. The process likewise makes it possible to produce the preferred particulate sizes of the glass powder as stated above and to filter out the particles of the stated sizes.

As described above, the grinding bodies preferably consist of the same material or of a material having the same refractive index as the starting material to be ground to form the glass powder.

It is preferable for the disruptive particles to be separated by passing the mixture of glass particulates and particles through a net and/or sieve, the mesh size of which corresponds to the minimum diameter of the particles to be separated.

The net and/or sieve acts in this case as it were as a filter for the disruptive particles. The net and/or sieve is distinguished by the presence of meshes through which the desired glass powder particulates can pass. If, in contrast thereto, use was made of a structure without open meshes, for example a woven fabric and/or felt, the glass powder particulates would likewise be able to collect thereon and would clog the filter in a very short time.

It is preferable for the net and/or sieve to be formed from fibres, similar to a fishing net. The fibres are preferably formed by polymer fibres, e.g. polypropylene, polytetrafluoroethylene, particularly preferably by polyamide.

A proven and preferred grinding process is a wet grinding process, in particular in stirred mills, as described in DE 4100604 C1. In the wet grinding process, a grinding slurry is produced in the mill. The disruptive particles can be separated as the grinding slurry circulates in the mill by inserting that filter into the mill in the case of which the mean particulate size of the glass particulates falls below the mesh size of the net and/or sieve. Alternatively, and preferably, the particles are separated by passing the grinding slurry through the net and/or sieve after completion of the grinding process. The disruptive particles remain in the net and/or sieve in both alternatives. To obtain the glass powder, the filtrated grinding slurry obtained, from which the disruptive particles have been separated, is usually dried in a subsequent step using suitable drying processes, e.g. freeze-drying processes.

The glass powder according to the invention and/or obtained by the described process is used with preference as a filler for a plastic dental composition, in particular for a dental composite. This similarly relates to the production of a plastic dental composition, in particular a dental composite.

In the application of the process according to the invention, the disruptive particles were separated by filtration using a net of monofilament polyamide formed as a filter bag which, depending on the desired particulate size of the glass powder particulates, had a clear mesh size of more than 1 µm and less than 15 µm. In comparative tests, it was determined that, in the case of a woven fabric, the particles accumulate at the surface of the woven fabric and clog it. In the case of relatively coarse woven fabrics, the particles formed by breaking out from the grinding bodies to some extent could no longer be restrained. When multifilament woven fabrics or needle felting were used, there was additionally a major risk of contamination with polymer fibres, which can become detached from the filter. Furthermore, more and more particles and/or glass powder particulates became caught in the multiply woven fabric over the course of filtration, which in turn led to clogging of the filter.

BRIEF DESCRIPTION OF THE FIGURES

The FIGURE shows a particle size distribution of the particles according to the present disclosure separated from a grinding slurry in the net and/or sieve.

DETAILED DESCRIPTION

The invention is explained in more detail with reference to the accompanying FIGURE. The FIGURE shows a particle size distribution of the particles separated from a grinding slurry in the net and/or sieve. The mesh size of the net and/or sieve was 5 µm. The maximum of the distribution, the form of which corresponds approximately to a Gaussian profile, is about 30 µm. That is to say, the mean particle size was about 30 µm. This had the effect that particles having a particulate size of 30 µm were no longer present in the glass powder.

The invention has the advantage over the prior art that it provides glass powder having a very homogeneous grain size distribution. In particular, disruptive large particles are not present in the glass powder according to the invention. The latter is therefore particularly suitable for use as a filler in plastic dental compositions and/or as a raw material for producing the latter, because the glass powder can be produced in very small mean particulate sizes without disruptive craters being formed in long-term use.

What is claimed is:

1. A process for producing a glass powder, comprising:
   wet grinding a starting material of glass in a mill with grinding bodies to produce a grinding slurry, the grinding bodies comprising a material that is the same as or has the same refractive index as the starting material to form a mixture of glass particulates and particles, and the grinding slurry having ground glass particles with a first particle distribution with a first mean particulate size of less than or equal to 1.5 µm and disruptive glass particles with a second mean particulate size of greater than 10 µm; and
   passing the grinding slurry through a net and/or sieve having a mesh size that corresponds substantially to a minimum diameter of the particles to be separated to remove the particles having a particle size of greater than 10 µm by separation, wherein the first particle distribution is preserved.

2. The process according to claim 1, wherein the net and/or sieve is formed of polymer fibres.

3. The process according to claim 1, wherein the net and/or sieve is formed of polyamide fibres.

4. The process according to claim 1, wherein the powder particulates have a mean particulate size of less than or equal to 1.0 µm.

5. The process according to claim 1, wherein the powder particulates have a mean particulate size of less than or equal to 0.7 µm.

6. The process according to claim 1, wherein the powder particulates have a mean particulate size of less than 0.5 µm.

7. The process according to claim 1, wherein the powder particulates have a mean particulate size of less than 0.25 µm.

8. The process according to claim 1, wherein the powder particulates are free of particles having a particle size of greater than 5 µm.

9. The process according to claim 1, wherein the powder particulates are free of particles having a particle size of greater than 3 µm.

10. The process according to claim 1, further comprising using the glass powder as a filler in a plastic dental composition.

11. A process for producing a glass powder, comprising:
    selecting grinding bodies comprising a material that is the same as or has the same refractive index as a starting material of glass;
    wet grinding the starting material in a mill with the grinding bodies to produce a grinding slurry having ground glass particles with a first particle distribution having a first mean particulate size of less than or equal to 1.5 µm and disruptive glass particles with a second mean distribution particulate distribution having a particulate size of greater than 10 µm; and
    passing the grinding slurry through a net and/or sieve having a mesh size sufficient to remove particles having a particle size of greater than 10 µm by separation.

12. The process according to claim 11, wherein the first particle distribution is preserved after passing the grinding slurry through a net and/or sieve.

\* \* \* \* \*